US005917068A

United States Patent [19]

Barnicki et al.

[11] Patent Number: 5,917,068

[45] **Date of Patent: *Jun. 29, 1999**

[54] POLYUNSATURATED FATTY ACID AND FATTY ACID ESTER MIXTURES FREE OF STEROLS AND PHOSPHORUS COMPOUNDS

[75] Inventors: Scott Donald Barnicki; Charles Edwan Sumner, Jr., both of Kingsport, Tenn.

[73] Assignee: Eastman Chemical Company, Kingsport, Tenn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/768,828

[22] Filed: Dec. 18, 1996

Related U.S. Application Data

[60] Provisional application No. 60/009,393, Dec. 29, 1995.

[51] Int. Cl.$^6$ .................................................. C07C 51/377

[52] U.S. Cl. .......................... 554/160; 554/163; 554/174

[58] Field of Search .................................... 554/160, 163, 554/174

[56] References Cited

U.S. PATENT DOCUMENTS

| | | |
|---|---|---|
| 4,104,286 | 8/1978 | Fallis et al. . |
| 4,670,285 | 6/1987 | Clandinin et al. . |
| 4,692,280 | 9/1987 | Spinelli et al. . |
| 4,698,185 | 10/1987 | Diijkstra et al. . |
| 4,857,236 | 8/1989 | Günther . |
| 5,084,215 | 1/1992 | Kearns et al. . |
| 5,091,117 | 2/1992 | Athnasios et al. . |
| 5,106,542 | 4/1992 | Traitler et al. . |
| 5,112,956 | 5/1992 | Tang et al. . |
| 5,130,061 | 7/1992 | Cornieri et al. . |
| 5,250,719 | 10/1993 | Tronconi . |
| 5,304,545 | 4/1994 | Mentink et al. . |
| 5,342,633 | 8/1994 | Cully et al. . |
| 5,616,359 | 4/1997 | Heidlas et al. . |
| 5,750,180 | 5/1998 | Heidlas et al. . |

FOREIGN PATENT DOCUMENTS

| | | |
|---|---|---|
| 0 610 742 | 8/1994 | European Pat. Off. . |
| 1559064 | 1/1978 | United Kingdom . |
| WO 80 02100 | 10/1980 | WIPO . |
| WO 89 11521 | 11/1989 | WIPO . |
| WO 91/03946 | 4/1991 | WIPO . |
| WO 94/21766 | 1/1994 | WIPO . |
| WO 96 14311 | 5/1996 | WIPO . |
| WO 97/26804 | 7/1997 | WIPO . |
| WO 97/27274 | 7/1997 | WIPO . |
| WO 97/27275 | 7/1997 | WIPO . |

OTHER PUBLICATIONS

Derwent Information Ltd., WPI Acc. No. 87–286816/198741. (JP 62198351 A).

Derwent Information Ltd., WPI Acc. No. 89–224485/198931 (JP 1160989 A).

Derwent Information Ltd., WPI Acc. No. 89–195153/198927 (JP 1131189 A).

Derwent Information Ltd., WPI Acc. No. 89–104000/198914 (JP 1051091 A).

Derwent Information Ltd., WPI Acc. No. 87–189773/198727 (JP 62120340 A).

Derwent Information Ltd., WPI Acc. No. 87–154908/198722 (JP 62093294 A).

Derwent Information Ltd., WPI Acc. No. 85–120199/198520 (JP 60061520 A).

Derwent Information Ltd., WPI Acc. No. 71–78570S/197150 (JP 71042186 B).

Derwent Information Ltd., WPI Acc. No. 92–364471/199244 (SU 1701737).

Derwent Information Ltd., WPI Acc. No. 96–357246/199636 (JP 8168390 A).

Derwent Information Ltd., WPI Acc. No. 95–348501/199545 (JP 7238293 A).

Derwent Information Ltd., WPI Acc. No. 87–061189/198709 (JP 62016439 A).

Derwent Information Ltd., WPI Acc. No. 84–198209/198432 (JP 59113099 A).

C. K. Han et al., *Korean J. Animal Sci.*, 33(8), pp. 602–606 (1991).

G.Zeidler et al., *Egg Uses and Processing Technologies; New Developments*, CAB International, pp. 115–127 (1994).

P. Banerjee et al., *Biochimica et Biophysica Acta*, 1110, pp. 65–74 (1992).

Database WPI, Section Ch, Week 9545, Derwent Publications, Ltd., London, GB; AN 95–348501 XP002030664 & JP 07 238 293 A(Bizen Kasei KK), Sep. 12, 1995 (see abstract).

Lanzani et al., J. Am. Oil Chem. Soc., 71 (1994) 609.

*Primary Examiner*—Paul J. Killos
*Attorney, Agent, or Firm*—Cheryl J. Tubach; Harry J. Gwinnell

[57] ABSTRACT

This invention relates to a process for removing sterols and phosphorous compounds from naturally occurring lipid mixtures. The process involves hydrolyzing a naturally occurring lipid mixture containing phospholipids, triglycerides, and sterols to form a two-phase product containing a fatty acid phase comprised of free fatty acids and sterols, and an aqueous phase comprised of water, glycerol, and glycerol phosphoric acid esters. The aqueous phase is separated from the fatty acid phase and the crude fatty acid phase is heated to convert the free sterols to fatty acid sterol esters. The free fatty acids are distilled from the fatty acid sterol esters to yield purified fatty acids which are free of cholesterol and other sterols, and phosphorous compounds.

37 Claims, No Drawings

POLYUNSATURATED FATTY ACID AND FATTY ACID ESTER MIXTURES FREE OF STEROLS AND PHOSPHORUS COMPOUNDS

CROSS REFERENCE TO RELATED APPLICATION

This application claims the benefit of provisional application Ser. No. 60/009,393, filed Dec. 29, 1995.

FIELD OF THE INVENTION

This invention relates to a process for preparing fatty acid and fatty acid ester mixtures high in polyunsaturated fatty acids, which are essentially free of cholesterol and other sterols, and phosphorus, and are derived from naturally occurring lipid mixtures.

BACKGROUND OF THE INVENTION

The n-6 family of polyunsaturated fatty acids, based on the parent linoleic acid and higher derivatives such arachidonic acid, have long been established as essential in human and animal nutrition. More recently, evidence has accumulated for the nutritional importance of the n-3 family of polyunsaturated fatty acids, based on the parent linolenic acid and higher derivatives such as eicosapentaenoic acid (EPA) and docosahexaenoic acid (DHA). These polyunsaturated acids are the precursors for prostaglandins and eicosanoids, a powerful group of compounds which produce diverse physiological actions at concentrations as low as 1 $\mu$g/l. The prostaglandins are known to influence blood clotting, inflammatory and anti-inflammatory response, cholesterol absorption, bronchical function, hypertension, visual acuity and brain development in infants, and gastric secretions, among other effects.

Various members of the n-3 and n-6 families of polyunsaturated acids are natural constituents of many foodstuffs. However these polyunsaturated acids, in particular the longer chain acids such as arachidonic acid, DHA, and EPA, are either intimately combined with undesirable components such as cholesterol or are unsuitable for food applications in their functional form.

In many natural vegetable and animal derived lipid mixtures the polyunsaturated fatty acids such as arachidonic acid, DHA, and EPA are found predominantly in the phospholipid fraction of the lipid mixture and may be recovered from phospholipid concentrates. There are numerous methods in the literature for recovering phospholipids from lipid mixtures. For example, U.S. Pat. No. 4,698,185 discloses a method of separating phospholipids from crude vegetable triglyceride mixtures. The method involves the addition of water in a mass ratio about equal to the mass of phospholipids present in the lipid mixture, with or without heating, and with or without co-addition of citric or phosphoric acid, to cause the phospholipids to hydrate and separate into a second phase.

Such degumming methods, however, were designed for the removal of 1 to 2 weight % phosopholipids from crude vegetable triglycerides and are not directly applicable to the purification of other natural lipid mixtures, such as egg yolk lipids because of the order of magnitude higher levels of phospholipids (30–40 wt %) in egg yolk lipids. Addition of a 1:1 mass ratio of water to phospholipid with large amounts of phospholipids present causes the formation of a stable emulsion which prevents phase separation. Moreover, sterols tend to partition between both the phospholipid and triglyceride phases. A clean separation of sterols from phospholipids is not possible. In addition, the phospholipids are natural surfactants and as such cannot be used directly in place of the triglyceride portion of a food preparation because of the differences in food functionality between an oily triglyceride and a surfactant phospholipid molecule.

Cholesterol and other sterols, and phosphorous compounds are natural constituents of animal and vegetable lipid mixtures. However, the presence of large amounts of cholesterol and other sterols, and phosphorous in the human body is considered by physicians to be deleterious, since cholesterol has been implicated as a factor in a number of diseases, especially atherosclerosis, in which deposits containing a high proportion of cholesterol are deposited in blood vessels. Cholesterol, however, is found in significant quantities in a wide variety of foodstuffs, being present in most animal fats and eggs, and consequently restrictions upon the cholesterol intake of patients necessitate prohibiting or greatly reducing the consumption of many foodstuffs which may introduce complications in ensuring that the patients receive a properly balanced diet meeting all nutritional requirements.

In order to help people to reduce their cholesterol consumption without major modifications in their diet, it is desirable to provide a process by which cholesterol and other sterol compounds (many of which can be metabolized to cholesterol or its derivatives) can be extracted from various foodstuffs, thereby producing low-cholesterol versions of such foodstuffs. However, the process must not introduce into the foodstuff any material which is not generally recognized as safe for use in foodstuffs. In addition, the process should remove from the foodstuff not only cholesterol itself but also cholesterol derivatives and other sterol compounds which can be metabolized in the body to cholesterol or derivatives thereof, and which thus affect cholesterol levels in the body. Furthermore, the process should leave the foodstuff in a form which is as close as possible to that of the original, high-cholesterol foodstuff. Finally, the cholesterol-removal process should not remove vitamins and other important nutrients of the foodstuff.

Numerous attempts have previously been made to provide a cholesterol-removal process which meets these exacting criteria. U.S. Pat. No. 4,692,280, discloses a process for the purification of fish oils in which the oil is extracted with supercritical carbon dioxide to remove cholesterol, together with odoriferous and volatile impurities. Such carbon dioxide extraction processes, however, suffer from the disadvantage that they must be operated under pressure to keep the carbon dioxide in the supercritical phase, which increases the cost of the apparatus required. In addition, such carbon dioxide extraction processes are not very selective in the removal of cholesterol, and thus remove valuable constituents of the foodstuff. In addition, the properties of some foodstuffs may be altered disadvantageously by contact with supercritical carbon dioxide; for example, in some cases the carbon dioxide removes flavoring and odiferous components which affect the taste and smell of the treated foodstuff.

U.S. Pat. No. 5,091,117 discloses a process for removing at least one sterol compound and at least one saturated fatty acid from a fluid mixture by contacting the fluid mixture with an activated charcoal. U.S. Pat. No. 5,091,117 states, however, in column 12, lines 4–19, that the process should not be used for removing cholesterol from materials, such as egg yolks, which contain a combination of cholesterol and proteins, since a significant adsorption of proteins and their constituent amino acids occurs on the charcoal.

British. Pat. No. 1,559,064 discloses a process for removing cholesterol from butter triglycerides by distillation.

However, Lanzani et al [*J. Am. Oil Chem. Soc.* 71, (1994) 609] determined that only 90% of the cholesterol could be removed using the process disclosed in British. Pat. No. 1,559,064 without seriously affecting the quality of the end product. Excessive time at the high temperatures needed for more complete cholesterol removal was found to cause cis-trans isomerization of the polyunsaturated fatty acids. The trans form of polyunsaturated fatty acids are considered undesirable in food products. Thus, complete removal of cholesterol is not possible by distillation.

Egg yolk is an example of a lipid mixture rich in polyunsaturated fatty acids including arachidonic acid and (all-cis)-4,7,10,13,16,19-docosahexaenoic acid (DHA) in which the polyunsaturated fatty acids are predominantly bound in the phospholipids and which contain high levels of cholesterol. It is desirable to provide a process for the manufacture of egg-derived fatty acids and fatty acid esters high in polyunsaturated fatty acids which removes cholesterol and phosphorous residues without degrading or causing cis-trans isomerization of the essential polyunsaturated fatty acids contained therein or the taste and flavor of foods prepared using such fatty acid and ester mixtures. Moreover, the process for the manufacture of the fatty acid and ester mixtures should use materials which are on the Generally Recognized As Safe (GRAS) list of the U.S. Food and Drug Administration in order for the final product to be used in foods.

SUMMARY OF THE INVENTION

The present invention relates to a process for preparing fatty acid and fatty acid ester mixtures high in polyunsaturated fatty acids, which are essentially free of cholesterol and other sterols, and phosphorus, and are derived from naturally occurring lipid mixtures. The sterols and phosphorus compounds have been removed without degrading or causing cis-trans isomerization of the essential polyunsaturated fatty acids contained therein or the taste and flavor of foods prepared using such lipid mixtures. Moreover, the process of the present invention uses materials which are on the Generally Recognized As Safe (GRAS) list of the U.S. Food and Drug Administration. The process comprises the steps of:

A) hydrolyzing a lipid mixture containing phospholipids, triglycerides, and sterols to form a two-phase product containing a fatty acid phase comprising free fatty acids and sterols, and an aqueous phase comprising water, glycerol, and glycerol phosphoric acid esters;

(B) separating the aqueous phase from the fatty acid phase of the two-phase product formed in Step (A);

(C) reacting the fatty acids with the sterols in the fatty acid phase from Step (B) at a temperature of 150° C. to 250° C. to form a mixture comprising sterol fatty acid esters and water; and (D) distilling the sterol fatty acid esters formed in Step (C) at a temperature of 130° C. to 250° C. and a pressure of $1 \times 10^{-3}$ kPa to 0.5333 kPa, to recover purified fatty acids which are free of cholesterol and other sterols, and phosphorous compounds; and optionally (E) reacting the purified fatty acids prepared in Step (D) with a monohydric or polyhydric alcohol in a molar ratio of 1 to 2 moles of fatty acid to each hydroxyl equivalent of the alcohol to produce a fatty acid ester.

DESCRIPTION OF THE INVENTION

The process of the present invention for preparing fatty acid and fatty acid ester mixtures high in polyunsaturated fatty acids, derived from naturally occurring lipid mixtures, and essentially free of cholesterol and other sterols, and phosphorous compounds involves up to five steps. As used herein, the phrase "essentially free of cholesterol, sterols, and phosphorous compounds" means that at least 95%, preferably at least 98%, of the cholesterol and other sterols, and phosphorous compounds are removed from the lipid mixture starting material by the process of the present invention. In the first step, Step (A), a lipid mixture containing phospholipids, triglycerides, and sterols is hydrolyzed in water to form a two-phase product containing a fatty acid phase comprised of free fatty acids and sterols, and an aqueous phase comprised of water, glycerol, and glycerol phosphoric acid esters.

Naturally occurring lipid mixtures high in polyunsaturated fatty acids are derived from animal and vegetable matter. Sources of lipid mixtures include: marine animals such as blue-colored fish, such as the mackerel, sardine, mackerel pike and herring; salmon; cod liver oil; animal marine plankton, such as krill and the various shrimp-like copepods; eggs; green leafy vegetables such as spinach, broccoli, and purslane; and oilseeds such as soya, sunflower, flax, canola, rapeseed, and cotton seeds. Any source of lipid mixtures high in polyunsaturated fatty acids may be used in the process of the present invention. The lipid mixture is separated from the animal or vegetable fat or oil by extraction or leaching with a solvent such as alcohol or hydrocarbon. For example, egg yolk powder may be mixed with methanol which yields a lipid mixture containing phospholipids, triglycerides, and sterols in liquid form, and solid protein material. The solid protein material is easily separated from the lipid mixture by methods known in the art such as filtration or centrifugation.

The hydrolysis of the lipid mixture in Step (A) may be catalyzed by either the addition of an acid or a base. Preferably, the hydrolysis of the lipid mixture in Step (A) is accomplished by a base-catalyzed hydrolysis reaction. Such base-catalyzed hydrolysis reactions are commonly known as a saponification reactions. Suitable base catalysts are aqueous alkali which include sodium, lithium, calcium, and potassium salt of an hydroxide, carbonate or bicarbonate. Combinations of base catalysts may also be used.

The hydrolysis reaction in Step (A) is an equilibrium-limited reaction. The base-catalyzed reaction is driven to completion through the formation of a metal salt of the corresponding fatty acid. The base catalyst is added in at least a stoichiometric amount up to two times the stoichiometric amount based on the equivalents of fatty acid groups contained in the lipid mixture. Preferably, the base catalyst is added in an amount of 1.1 to 1.5 times the equivalents of fatty acid groups contained in the lipid mixture.

In a base-catalyzed hydrolysis the metal salts of fatty acids formed during hydrolysis are acidified to a pH of 4 or less with a mineral acid to form a two-phase product containing a fatty acid phase comprised of free fatty acids and sterols, and an aqueous phase comprised of water, glycerol, and glycerol phosphoric acid ester residues.

Mineral acids useful for the acidification of the metal salts of the fatty acids must have a pKa lower than the pKa of the free fatty acid. Suitable mineral acids include sulfuric acid, nitric acid, hydrochloric acid, and phosphoric acid. Combinations of mineral acids may also be used. The mineral acid is added in at least a stoichiometric amount based on the amount of base catalyst. The mineral acid may be added in dilute or concentrated form. A preferred mineral acid is aqueous hydrochloric acid.

Unreacted phospholipids and hydrolyzed phospholipid residues act as surfactants and may interfere with the formation of distinct fatty acid and aqueous phases in Step (A). A lower alkyl alcohol having 1 to 4 carbon atoms may be added to the hydrolysis product in Step (A) to assist in two-phase formation. The alcohol solubolizes the fatty acids and helps partition the surfactant residues into the aqueous phase. The alcohol is added at a 0.5:1 to 3:1, preferably a 1.5:1 mass ratio of alcohol to phospholipid present in the lipid mixture fed to Step (A). Examples of a lower alkyl alcohol suitable to aid in two-phase formation include methanol, ethanol, propanol, isopropanol, isobutanol, and butanol.

Preferably, a lower alkyl alcohol having 1 to 4 carbon atoms is added to the lipid mixture before the water and catalyst are added for the hydrolysis reaction in Step (A). The addition of the alcohol before hydrolysis causes the formation of two liquid phases when the temperature is maintained between 30° C. to 60° C., preferably 40° C. to 50° C. The top phase is comprised of phospholipids, sterols, and alcohol, the bottom phase is comprised of triglycerides and sterols. The triglyceride phase is removed by methods known in the art such as decantation. For lipid mixtures such as egg yolks in which the polyunsaturated fatty acids such as arachidonic acid, DRA, and EPA are predominantly bound in the phospholipids rather than the triglycerides, the addition of the alcohol is a convenient and inexpensive method of removing the triglycerides and concentrating the polyunsaturated fatty acids in the remaining lipid mixture. The addition of the alcohol does not interfere with the subsequent hydrolysis reaction.

Examples of lower alkyl alcohols suitable for the formation of separate triglyceride and phospholipid phases include methanol, ethanol, propanol, isopropanol, isobutanol, and butanol. If an alcohol is added before the hydrolysis in Step (A), the alcohol is added in a mass ratio of 0.5:1 to 3:1 alcohol to lipid mixture. Preferably, the alcohol is added in a mass ratio of 1:1 to 2:1 alcohol to lipid mixture. The addition of alcohol outside this range either does not result in the formation of a two phase mixture or results in poor partitioning of triglycerides and phospholipids into their respective phases.

In the second step, Step (B), the aqueous phase is separated from the fatty acid phase of the two-phase product formed in Step (A). The aqueous phase is removed by methods known in the art such as decantation. It is important to note that at acidic pH, the fatty acids may form fatty acid alcohol esters with any lower alkyl alcohol added optionally in Step (A). The fatty acid alcohol esters are undesirable as they represent a yield loss of fatty acids. Therefore, it is desirable that: (1) the two-phase product formed in Step (A) be maintained at a low a temperature to slow the esterification reaction, but at a temperature which maintains the fatty acids as a liquid phase, between 35° C. to 55° C., preferably 40° C. to 50° C.; and (2) the aqueous phase should be removed as soon as practical from the two-phase product.

In the third step, Step (C), the fatty acid phase from Step (B) is heated at a temperature of 150° C. to 250° C., preferably 170° C. to 230° C., most preferably 200° C. to 230° C., to allow the fatty acids to react with the sterols to form sterol fatty acid esters and water. Optionally water is removed from the reaction to drive the equilibrium toward the formation of the sterol fatty acid esters. The formation of fatty acid sterol esters represents a yield loss of fatty acids, including a statistical distribution of polyunsaturated fatty acids based on their percentage in the mixture, equal to one mole of fatty acid for each mole of sterol ester formed. This yield loss is necessary in order to convert the sterols into sterol esters which can be separated easily from fatty acids.

Optionally an esterification catalyst can be added in Step (C) to increase the rate of sterol fatty acid ester formation. Examples of suitable esterification catalysts include: dibutyl tin oxide, phosphoric acid, zinc oxide, hydrochloric acid, and butyl stannoic acid.

In the fourth step, Step (D), the fatty acid and sterol ester mixture formed in Step (C) is distilled at a temperature of 130° C. to 250° C. and a pressure of $1\times10^{-3}$ kPa to 0.5333 kPa, to recover purified fatty acids. The distillation is preferably conducted at a temperature of 180° C. to 220° C. and a pressure of $1\times10^{-3}$ kPa to 0.0667 kPa. The fatty acids are relatively volatile and distill overhead, while the sterol fatty acid esters are not volatile and remain with the residue. The molecular weight distribution of the fatty acid residues of subsequently derived glyceride products can be controlled by distillation. For example, the lower molecular weight fatty acids tend to be the lower boiling fatty acids and concentrate in the first fractions of the distillation; and the higher molecular weight acids are found in the higher boiling fractions. The resulting fatty acids are essentially free of sterol compounds and phosphorous containing residues. Successive distillation stages may be used to remove lighter acids and concentrate heavier polyunsaturated acids such as arachidonic, DHA, and EPA.

The formation of sterol fatty acid esters are critical to the present invention in order to recover fatty acids in high yield which are free of sterols and sterol esters. The relative volatility between the high molecular weight polyunsaturated fatty acids such as arachidonic acid, DHA, and EPA, and the sterol esters is relatively large. Thus, the polyunsaturated fatty acids can be separated sharply from the sterol esters with any single equilibrium stage, non-refluxed high vacuum distillation apparatus known in the art, including a wiped-film evaporator, a falling film evaporator, a short path evaporator, and a centrifugal molecular still.

Alternatively, the relative volatility of the free sterols and the high molecular weight polyunsaturated fatty acids such as arachidonic acid, DHA, and EPA, is relatively small. Thus, a sharp separation of free sterols from higher molecular weight polyunsaturated fatty acids is not practical by single equilibrium stage, non-refluxed high vacuum distillation methods.

Multistage fractional distillation devices with reflux which are capable of sharp separations between components of low relative volatility such as free sterols and fatty acids must operate at higher pressures and subsequently higher temperatures in order to allow for sufficient pressure drop across the multistage column. The requisite higher temperatures required in a multistage distillation leads to undesirable heat degradation and cis-trans isomerization of the unsaturated fatty acids.

Other methods of separation of sterols such as crystallization or supercritical extraction are more difficult and expensive. The melting points of sterols and fatty acids overlap and a sharp separation requires complicated, expensive fractional crystallization equipment and refrigeration. Supercritical extraction requires expensive high pressure equipment to maintain the extractant at supercritical conditions.

Optionally, the purified fatty acids, free of sterols and phosphorous containing residues, from Step (D) may be mixed with a C1-C10 alkyl monohydric or polyhydric alcohol and heated to produce a fatty ester of the alcohol, Step (E). Suitable monohydric alcohols include, for example, methanol, ethanol, propanol, isopropanol, and butanol. Suitable polyhydric alcohols include, for example, glycerin, propylene glycol, ethylene glycol, sorbitol, sucrose, erythritol, pentaerythritol, mannitol, fructose, glucose, xylitol, and lactitol. The monohydric or polyhydric alcohol is added in a molar ratio of 1 to 2 moles of fatty acid to each hydroxyl equivalent of the alcohol. Preferably, in a molar ratio of 1.1 to 1.3 moles of fatty acid to each hydroxyl equivalent of the alcohol. Optionally, water may be removed during the esterification reaction to drive the equilibrium toward the ester product.

The following examples are intended to illustrate, but not limit, the scope of this invention. All parts and percentages in the examples are on a weight basis unless otherwise stated.

EXAMPLE 1

A 500 mL three neck flask equipped with a mechanical stirrer, reflux condenser, addition funnel, thermowell, heating mantle, and nitrogen atmosphere was charged with 154 grams of lipid mixture, obtained by the leaching of powdered egg yolk with methanol, 193 grams of methanol, and 28 grams of water. Sodium hydroxide (80 grams of 50% solution) was added through the addition funnel. The resulting mixture was heated at 64° C. for 145 minutes. Hydrochloric acid (84 mL of 12 N) was added over five minutes. An additional 14 mL of HCl was added in small portions until a pH of 2 was attained. Stirring was stopped and the phases were allowed to separate. The aqueous (bottom) phase was separated and contained 0.58% phosphorous. The organic phase weighed 128 grams, and contained 6% monoglycerides, 2% fatty acid methyl esters, 5% cholesterol, and free fatty acids.

The free fatty acids, 124 grams, were charged to a 300 mL 3 neck flask equipped with a mechanical stirrer, water trap, thermowell, heating mantle, and a sparge tube. The mixture was heated at 170° C. for 4 hours with a nitrogen sparge of 100 mL/min. Residual methanol, 14 grams, and water of reaction were collected. The resulting product was distilled at 245° C. and 0.5 Torr (0.0667 kPa) on a wiped film evaporator to give 83 grams of distillate and 16 grams residue. The distillate (fatty acids) contained 0.13% cholesterol and no detectable phosphorous. The residue contained predominantly cholesterol esters of fatty acids.

A sample of the distillate fatty acids, 67 grams, was charged to a 300 mL 3 neck flask equipped with a mechanical stirrer, water trap, thermowell, heating mantle, reflux condenser, and sparge tube. The sample was warmed to 110° C., and 6.6 grams of glycerin was added under nitrogen. The temperature was increased to 160° C. The resulting mixture was heated for 29 hours with a nitrogen sparge of 100 mL/min. The resulting product was passed through a wiped film evaporator at 0.4 Torr and 220° C. to remove excess fatty acids. The fatty acid distillate weighed 8 grams, and the triglyceride residue weighed 50 grams. Analysis of the triglycerides showed 96% triglycerides and 4% diglycerides. Total cholesterol was less than 0.13%.

EXAMPLE 2

A 22 L reaction vessel was charged with 7733 grams of the methanol containing phase obtained from leaching 5 kg of powdered egg yolk with 9 L of methanol at 60° C. for 3 hours. The mixture was heated to reflux and 5.7 L of methanol was distilled off. To the resulting mixture was added 2.5 L of water, followed by 750 grams of 50% NaOH solution. The resulting mixture was heated at reflux (65–70° C.) with stirring for 2.5 hours. The heat was removed, and 785 mL of conc. HCl was slowly added while the temperature of the mixture was maintained above 50° C. Agitation was discontinued, and the phases were allowed to separate. The bottom phase was separated and weighed 5764 grams and contained 0.31% phosphorous. The fatty acid phase weighed 1350 grams and contained 5.2% cholesterol, 0.17% phosphorous, and 5.5% fatty acid methyl esters. The fatty acid phase was charged to a 3 L flask equipped with a N2 sparge and water trap and was heated to 170° C. for 7 hours with a sparge rate of about 1 L/min. A total of 83 grams of methanol after mixture was collected during this time. The product weighed 1216 grams and contained 0.02% cholesterol.

The product was purified by distillation through a wiped film evaporator. Distillation at 180° C. and 0.5 Torr gave 215 grams of distillate that contained 13% fatty acid methyl esters, 41% palmitic acid, and 24% oleic acid. The residue was redistilled at 280° C. to give 745 grams of distillate and 151 grams of residue. The residue contained mainly cholesterol esters. The distillate contained a larger fraction of higher molecular weight fatty acids than the crude material.

A 2 L flask equipped with a N2 sparge and water trap was charged with 708 grams of the distillate obtained at 280° C. and with 71 grams of glycerin. The resulting mixture was heated at 160° C. for 24 hours. The resulting product was transferred to the wiped film evaporator and distilled at 280° C. and 0.5 Torr to give 155 grams fatty acid distillate and 480 grams of triglyceride product. The triglyceride product contained 90% triglycerides and 9% diglycerides.

EXAMPLE 3

A 300 mL flask equipped with a mechanical stirrer, water trap, and N2 sparge was charged with 80.5 grams of fatty acid distillate recovered from Example 2, and with 7.82 grams of glycerin. The resulting mixture was heated at 230° C. with a N2 sparge for 3 hours. The mixture contained 86% triglycerides and 12% diglycerides.

EXAMPLE 4

The procedure described in Example 2 was followed except the methanol was not distilled from the saponification step until after the NaOH was added. A 6060 grams methanol solution of lipid mixture was mixed with 750 grams of 50% NaOH. The resulting mixture was heated at reflux while 2 L of methanol was distilled from the mixture over a 150 minutes. Water, 200 mL, was added back to the mixture and heating was continued an additional 30 minutes. The mixture was acidified to pH of 2 and was allowed to cool to 60° C. over a two hour period and the phases were separated. The fatty acid phase weighed 771 grams and contained 20% fatty acid methyl esters.

EXAMPLE 5

A 500 mL flask was charged with 83 grams of an egg lipid mixture free of methanol, 122 mL of water, and 39 grams of 50% NaOH solution. The resulting mixture was heated at 70° C. for 3 hours. Concentrated HCl (41 mL) was added over five minutes, causing a slight exotherm. The addition of HCl caused the product to form as a sticky, solid phase which could not be cleanly separated from the aqueous phase. Methanol, 122 grams, was added to the mixture at 60° C. while stirring. The resulting mixture was transferred to a warm separatory funnel and the phases were allowed to separate. The aqueous phase weighed 343 grams and the fatty acid phase weighed 65.6 grams. The fatty acid product contained less than 2% fatty acid methyl esters.

EXAMPLE 6

A 1213 gram sample of fatty acids that had been treated to esterify cholesterol was charged to a steam jacketed addition funnel. The material was fed to a Rodney-Hunt wiped film molecular still at a rate of 5 mL/min. The temperature of the still was maintained at 150° C. and the pressure was 0.5 Torr. A total of 215 grams of distillate was collected. The distillate contained 41% palmitic acid, 24% oleic acid, 13% fatty acid methyl esters, and less than 0.5% of C20 fatty acids. The residue was charged to the addition funnel and fed to the molecular still at a rate of 3.5 mL/min while the temperature of the still was maintained at 230° C. and the pressure was 0.4 Torr.

The distillate weighed 547 grams and contained 45% oleic acid, less than 1% fatty acid methyl esters, and greater than 3% of C20 and heavier fatty acids. The residue from this fraction was charged to the addition funnel and fed to the molecular still at a rate of 3.5 mL/min while the temperature was maintained at 250° C. and the pressure was 0.35 Torr. The distillate weighed 193 grams and contained 47% oleic acid, no fatty acid methyl esters, and greater than 4% of C20 and heavier fatty acids. The residue weighed 151 grams and contained mainly fatty acid sterol esters and less than 2% free fatty acids.

EXAMPLE 7

A 1000 gal glass-lined reactor equipped with a mechanical agitator, condenser, nitrogen sparge, and vacuum system was charged with 1000 lb of egg yolk powder and 300 gal of methanol. The resulting mixture was heated to 65° C. and agitated for three hours. After filtering off the protein residue and washing with methanol, the methanol-lipid filtrate was returned to the 2000 gal reactor and heated with agitation to 45° C. The agitation was stopped and the mixture was allowed to settle for one hour, with the temperature maintained between 40–45° C. Phase separation spontaneously occurred. The bottom phase was decanted off, sampled, and weighed. Analysis showed the bottom phase to weigh 96 lb and contain 94.9% triglyceride, 509 ppm phosphorus, and a fatty acid distribution on a relative basis of 0.6% arachidonic acid and 0% DHA. The top phase, upon stripping off methanol, weighed 245 lbs, and contained 4% triglycerides, 3.63% phosphorus, and a fatty acid distribution on a relative basis of 6.5% arachidonic acid and 2.0% DHA.

Many variations will suggest themselves to those skilled in this art in light of the above detailed description. All such obvious modifications are within the full intended scope of the appended claims.

What is claimed is:

1. A process for preparing fatty acids and fatty acids esters essentially free of cholesterol, sterols, and phosphorous compounds from naturally occurring lipid mixtures, said process comprising the steps of:

(A) hydrolyzing a lipid mixture containing phospholipids, triglycerides, and sterols to form a two-phase product containing a fatty acid phase comprised of free fatty acids and sterols, and an aqueous phase;

(B) separating the aqueous phase from the fatty acid phase of the two-phase product formed in Step (A);

(C) reacting the fatty acids with the sterols in the fatty acid phase from Step (B) to form a mixture comprising sterol fatty acid esters and water; and (D) distilling the sterol fatty acid esters formed in Step (C) to recover purified fatty acids which are essentially free of cholesterol and other sterols, and phosphorous compounds.

2. A process for preparing fatty acids and fatty acids esters essentially free of cholesterol, sterols, and phosphorous compounds from naturally occurring lipid mixtures, said process comprising the steps of:

(A) hydrolyzing a lipid mixture containing phospholipids, triglycerides, and sterols to form a two-phase product containing a fatty acid phase comprised of free fatty acids and sterols, and an aqueous phase comprised of water, glycerol, and glycerol phosphoric acid esters;

(B) separating the aqueous phase from the fatty acid phase of the two-phase product formed in Step (A);

(C) reacting the fatty acids with the sterols in the fatty acid phase from Step (B) at a temperature of 150° C. to 250° C. to form a mixture comprising sterol fatty acid esters and water; and (D) distilling the sterol fatty acid esters formed in Step (C) at a temperature of 130° C. to 250° C. and a pressure of $1\times10^{-3}$ kPa to 0.5333 kPa, to recover purified fatty acids which are free of cholesterol and other sterols, and phosphorous compounds; and (E) reacting the purified fatty acids prepared in Step (D) with a C1–C10 alkyl monohydric or polyhydric alcohol in a molar ratio of 1:1 to 1:2 of moles of fatty acid to each hydroxyl equivalent of the alcohol to produce a fatty acid ester.

3. A process for preparing fatty acids and fatty acids esters essentially free of cholesterol, sterols, and phosphorous compounds from egg yolk, said process comprising the steps of:

adding a lower alkyl alcohol having 1 to 4 carbon atoms to egg yolk to form a phospholipid phase containing phospholipids, sterols and alcohol and a triglyceride phase containing triglycerides, at a temperature of 30° C. to 60° C., provided the alcohol is added in a mass ratio of 0.5:1 to 3:1 alcohol to egg yolk;

decanting the triglyceride phase;

hydrolyzing the phospholipid phase in the presence of an aqueous alkali to form a soap;

acidifying the soap by the addition of a mineral acid to a pH<4 to form a two-phase product containing a fatty acid phase comprised of free fatty acids and sterols, and an aqueous phase comprised of water, glycerol, and glycerol phosphoric acid esters;

separating the aqueous phase from the fatty acid phase of the two-phase product;

reacting the fatty acids with the sterols in the fatty acid phase at a temperature of 150° C. to 250° C. to form a mixture comprising sterol fatty acid esters and water;

distilling the sterol fatty acid esters at a temperature of 130° C. to 250° C. and a pressure of $1\times10^{-3}$ kPa to 0.5333 kPa, to recover purified fatty acids which are free of cholesterol and other sterols, and phosphorous compounds; and reacting the purified fatty acids with a C1-C10 alkyl monohydric or polyhydric alcohol in a molar ratio of 1:1 to 1:2 of moles of fatty acid to each hydroxyl equivalent of the alcohol to produce a fatty acid ester.

4. The process of claim 1 wherein the hydrolysis is base-catalyzed by an aqueous alkali selected from the group consisting of the sodium, calcium, lithium, and potassium salt of an hydroxide, carbonate, and bicarbonate, to form a metal soap of the fatty acid.

5. The process of claim 4 wherein the aqueous alkali is added in at least a stoichiometric amount up to two times the stoichiometric amount based on the equivalents of fatty acid groups contained in the lipid mixture.

6. The process of claim 4 wherein the aqueous alkali is added in an amount of 1.1 to 1.5 times the equivalents of fatty acid groups-contained in the lipid mixture.

7. The process of claim 4 wherein the metal soap of the fatty acid formed in the base-catalyzed hydrolysis of Step (A) is acidified at a pH<4 to a free fatty acid by the addition of a mineral acid.

8. The process of claim 1 wherein the hydrolysis product of Step (A) additionally contains a lower alkyl alcohol having 1 to 4 carbon atoms in a mass ratio of 0.5:1 to 3:1 alcohol to phospholipids contained in the naturally occurring lipid mixture.

9. The process of claim 8 wherein the lower alkyl alcohol is present in a mass ratio of 1:1 to 2:1 alcohol to phospholipids contained in the naturally occurring lipid mixture.

10. The process of claim 9 wherein the lower alkyl alcohol is methanol.

11. The process of claim 1 wherein a lower alkyl alcohol having 1 to 4 carbon atoms is added to the naturally occurring lipid mixture in a mass ratio of 0.5:1 to 3:1 alcohol to lipid which results in formation of a triglyceride phase and a phospholipid phase.

12. The process of claim 11 wherein the triglyceride phase is separated from the phospholipid phase by decantation prior to hydrolysis.

13. The process of claim 1 wherein the aqueous phase in Step (B) is separated from the fatty acid phase by decantation.

14. The process of claim 1 wherein Step (C) is conducted at a temperature of 200° C. to 230° C.

15. The process of claim 1 wherein an esterification catalyst is added in Step (C).

16. The process of claim 15 wherein the esterification catalyst is selected from the group consisting of dibutyl tin oxide, phosphoric acid, hydrochloric acid, zinc oxide, and butyl stannoic acid.

17. The process of claim 1 wherein the distillation in Step (D) is conducted at a temperature of 180° C. to 220° C. and a pressure of $1\times10^{-3}$ kPa to 0.0667 kPa.

18. The process of claim 2 wherein the purified fatty acids from Step (D) are esterified with a polyhydric alcohol selected from the group consisting of glycerin, propylene glycol, ethylene glycol, sorbitol, sucrose, erythritol, pentaerythritol, mannitol, fructose, glucose, xylitol, and lactitol.

19. The process of claim 2 wherein the purified fatty acids from Step (D) are esterified with a monohydric alkyl alcohol selected from the group consisting of methanol, ethanol, propanol, isopropanol, and butanol.

20. The process of claim 1 wherein said fatty acids and fatty acid esters contain less than about 2 weight percent of at least one of cholesterol, sterol and phosphorous compounds.

21. The process of claim 1 wherein said lipid mixture is hydrolyzed in water.

22. The process of claim 1 wherein said aqueous phase includes water, glycerol and glycerol phosphoric acid esters.

23. The process of claim 1 wherein said lipids are derived from animal and vegetable matter.

24. The process of claim 23 wherein said lipids are derived from fish, eggs, and vegetable matter.

25. The process of claim 24 wherein said lipids are derived from the egg yolk.

26. The process of claim 3 wherein at least a stoichiometric amount to about twice the stoichiometric amount of said aqueous alkali is added for hydrolyzing the phospholipid phase.

27. The process of claim 26 wherein the amount of said aqueous alkali added to said phospholipid phase is from about 1.1 to about 1.5 based on the equivalents of fatty acid groups contained in the lipid mixture.

28. The process of claim 3 wherein said mineral acid has a pKa lower than the pKa of the fatty acid.

29. The process of claim 3 wherein said mineral acid is selected from the group consisting of sulfuric acid, nitric acid, hydrochloric acid, phosphoric acid and combinations thereof.

30. The process of claim 1 wherein said reacting fatty acids with said sterols of Step (C) is at a temperature of about 150° C. to about 250° C.

31. The process of claim 30 wherein said reacting is at a temperature of about 170° C. to about 230° C.

32. The process of claim 31 wherein said reacting is at a temperature of about 200° C. to about 230° C.

33. The process of claim 1 wherein said distilling of said sterol fatty acid esters is at a temperature of about 130° C. to about 250° C. and at a pressure of about $1\times10^{-3}$ kPa to about 0.5333 kPa.

34. The process of claim 33 wherein said distilling is at a temperature of about 180° C. to about 220° C. and a pressure of $1\times10^{-3}$ kPa to about 0.0667 kPa.

35. The process of claim 1 wherein said purified fatty acids include arachidonic acid, eicosapentaenoic acid and docosahexaenoic acid.

36. The process of claim 2 wherein said fatty acids of Step (D) are reacted with said alcohol in a molar ratio of 1:1 to 1:3 moles of fatty acid to each hydroxyl equivalent of alcohol.

37. The process of claim 2 wherein said fatty acid esters include from about 3 weight percent to about 10 weight percent arachidonic acid and from about 0.1 weight percent to about 5 weight percent DHA.

* * * * *

UNITED STATES PATENT AND TRADEMARK OFFICE
CERTIFICATE OF CORRECTION

PATENT NO. : 5,917,068
DATED : June 29, 1999

INVENTOR(S) : Scott Donald Barnicki, Charles Edwan Sumner, Jr., Robert Alan Miller, Terrence Bruce Mazer It is certified that error appears in the above-identified patent and that said Letters Patent is hereby corrected as shown below:

Title page,
Item [75], Inventors:, add --- Robert Alan Miller, Columbus, Ohio; Terrence Bruce Mazer, Reynoldsburg, Ohio ---

Signed and Sealed this

Seventh Day of August, 2001

*Attest:*

Nicholas P. Godici

*Attesting Officer*

NICHOLAS P. GODICI
*Acting Director of the United States Patent and Trademark Office*